United States Patent [19]
Peterson et al.

[11] Patent Number: 6,063,980
[45] Date of Patent: May 16, 2000

[54] HIGH COMFORT CAST LINER

[75] Inventors: Robert Howe Peterson, Hendersonville, Tenn.; Kenneth Ashley Saum, Newark, Del.

[73] Assignee: E. I. du Pont de Nemours and Company, Wilmington, Del.

[21] Appl. No.: 09/072,617

[22] Filed: May 5, 1998

Related U.S. Application Data

[60] Provisional application No. 60/045,876, May 5, 1997.

[51] Int. Cl.⁷ ....................................................... A61F 13/00
[52] U.S. Cl. ................................................ 602/49; 602/44
[58] Field of Search .................................... 602/6, 43, 44, 602/48, 41, 49

[56] References Cited

U.S. PATENT DOCUMENTS

| | | | |
|---|---|---|---|
| 3,616,156 | 10/1971 | Scholl . | |
| 3,914,488 | 10/1975 | Gorrafa | 428/397 |
| 4,634,625 | 1/1987 | Franklin | 428/258 |
| 4,707,407 | 11/1987 | Clark et al. | 428/361 |
| 5,350,625 | 9/1994 | Peterson et al. | 428/219 |
| 5,433,987 | 7/1995 | Peterson et al. | 428/137 |

*Primary Examiner*—John G. Weiss
*Assistant Examiner*—Kevin Hart

[57] ABSTRACT

This invention relates to a cast liner that provides improved comfort over prior known cast liners. The cast liner provides several layers of material having functions which functionally complement one another. The inner layer comprises a soft highly breathable material with a first layer comprising a high wicking nonwoven material overlying the inner layer and a second layer comprising a stitch bond fabric which is relatively stiff but open and compressible to support the body through the underlying inner and first layers.

15 Claims, 1 Drawing Sheet

HIGH COMFORT CAST LINER

This application claims priority to Ser. No. 60/045,876 filed May 5, 1997.

FIELD OF THE INVENTION

This invention relates to materials placed against a living body and more particularly to materials placed against a human body for an extended period of time.

BACKGROUND OF THE INVENTION

It is generally known that part of the medical treatment for a broken bone is to stabilize or immobilize that portion of the body with a cast. Casts have traditionally been formed of a plaster material which is applied "wet" and cures in place. When it is to be removed, it must be cut with a tool. If the need for a cast continues, a new cast must be formed on the patient and cured. Such casts have traditionally been hot and uncomfortable.

Newer casts are being developed for wrapping portions of the body which are easily put on and taken off. These types of casts are often secured by hook and loop fastening systems and allow access to the injured area for treatment or examination by medical personnel. These casts allow the body to be cleaned and the materials directly in contact with the body to be replaced. Current materials used in contact with the body include a wool fleece or liner. The fleece, however, still tends to be hot and uncomfortable.

The comfort of the wearer tends to be a greater problem for casts that are applied to the torso as compared to casts for arms or legs. For example, a patient who has undergone open heart surgery generally wears an orthopedic vest while the body, such as the sternum and ribs, mends. The vest surrounds the upper torso down at least approximately to the waist. Such a cast may allow for periodic cleaning which may be quite appreciated by the patient, but the feeling of comfort inside the cast is still of considerable concern for the patient.

Accordingly, it is an object of the present invention to provide a cast liner which overcomes the above noted limitations and disadvantages of the prior art.

It is a further object of the present invention to provided a cast liner which provides greater comfort for the patient while serving the medical needs.

SUMMARY OF THE INVENTION

The aforementioned objects of the invention are accomplished by a cast liner comprising a first layer of spunlaced hydroentangled nonwoven fabric comprising a blend of fiber wherein one fiber is an acrylic material and the second fiber is a synthetic cellulosic. The second layer is at least about a five ounce per square yard high loft fabric formed of at least about 10 denier fiber.

BRIEF DESCRIPTION OF THE DRAWINGS

The invention will be more easily understood by a detailed explanation of the invention including drawings. Accordingly, drawings which are particularly suited for explaining the invention are attached herewith; however, it should be understood that such drawings are for explanation only and are not necessarily to scale. The drawings are briefly described as follows.

DETAILED DESCRIPTION OF THE PREFERRED EMBODIMENT

Figure 1:
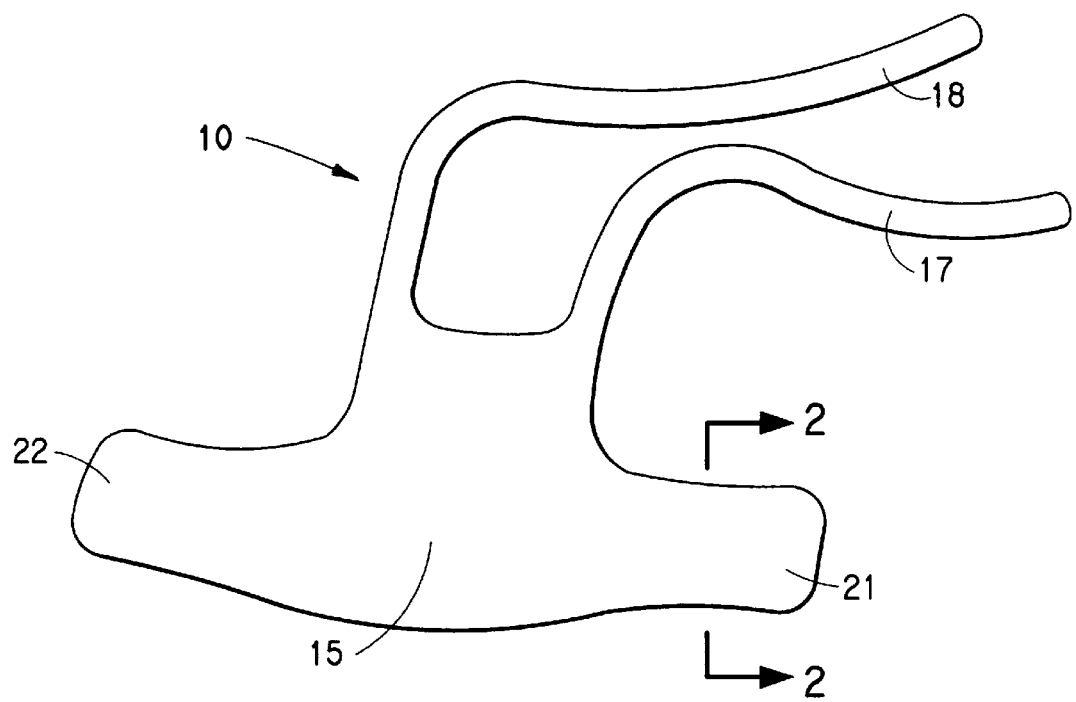
FIG. 1 is a perspective view of orthopedic vest which is a preferred embodiment of the present invention.

Referring now to the drawings, there is shown in FIG. 1, an orthopedic vest 10 which is comprised of a main body portion 15 suited for covering the chest and abdomen of a patient or wearer. The vest 10 further includes shoulder straps 17 and 18 extending upwardly from the opposite upper corners of the main body portion 15. Waist panels 21 and 22 are arranged to extend from the main body portion of the vest 10 around the sides and back portion of the wearer at about the patient's waist. The waist panels 21 and 22 and shoulder straps 17 and 18 include hook and loop fasteners so that the vest 10 may be secured about the patient to provide the support, immobilization or protection as desired by the medical practitioner.

Figure 2:
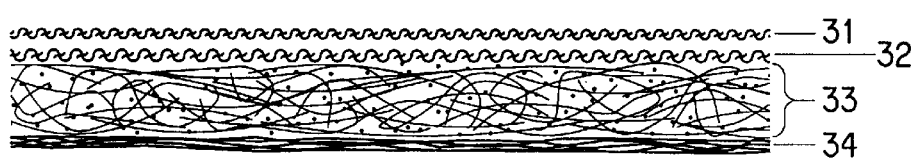
FIG. 2 is an enlarged cross section view taken along Line 2—2 of FIG. 1 showing the layers of the vest.

The vest 10 is constructed of several layers of material as shown in FIG. 2. Specifically, there is an inner layer 31 which is provided for comfort of the patient. Preferably, the inner layer 31 is a soft, highly breathable material which is able to transport moisture laterally away from the source. In the preferred embodiment, the inner layer 31 is approximately 1.0 to 5.0 ounce per square yard knit fabric wherein the fiber has a cross section suited for wicking moisture. It is noted that these references disclose fibers having a scalloped-oval cross-section. Such a cross-section is desirable because moisture can wick or transport along the channels in the fiber. A preferred example of such fibers are Coolmax® fibers which are sold by E. I. du Pont de Nemours and Company of Wilmington Del. (DuPont) and are described in U.S. Pat. Nos. 3,914,488, 4,634,625 and 4,707,407. Such fibers are used in performance fabrics for wicking moisture such as athletic apparel.

A first layer 32 which is adjacent to the inner layer 31 is made of a spunlaced nonwoven fabric having high wicking, high comfort qualities. The first layer is preferably a 1.5 to 4.0 ounce per square yard nonwoven fabric marketed under the tradename ComforSorb® XM fabric sold by DuPont. The preferred fabric is disclosed and described in U.S. Pat. Nos. 5,350,625 and 5,433,987 to Summers and Peterson which are incorporated herein by way of reference. The material basically comprises a blend of acrylic and synthetic cellulosic fibers wherein crimped acrylic fibers having a denier per filament (dpf) of about 0.75 to about 3.0 and a length from about 0.75 to about 3.0 inches comprises about 25 percent, but less than 50 percent, by weight of the second layer 32 with the remainder being crimped, synthetic, hydrophilic cellulosic fibers having a dpf of from about 0.75 to about 3.0 and a length from about 0.75 to about 3.0 inches. The acrylic fiber is preferably pack resistant to provide loft while the cellulosic fibers are hydrophilic. The acrylic fibers may alternatively be substituted with polypropylene or acetate polymer fibers.

The first fabric layer 32 wicks moisture from the inner layer so that the patient has a dry and fresh feeling fabric against the skin. Thus, the water-wicking and water transporting properties of the first layer 32 are important for best results. The first layer 32 has the best water-wicking and transport properties when the fabric consists essentially of 30 to 40% of the acrylic fibers and correspondingly 70 to 60% of the cellulosic fibers and has a basis weight of 3.0 to 5.0 oz/yd$^2$. For best performance, the cellulosic fibers consist essentially of solvent spun unmodified cellulose, as opposed to those made using regenerated xanthated cellulose, commonly known as viscose rayon.

Both the synthetic hydrophilic unmodified cellulosic fibers and the acrylic fibers are preferably of non-round cross-section for the best wicking and transport performance, and especially those having a known crenulated cross-section. Also, substantially round cross-sections can be used which can provide bulk. The acrylic fibers are comprised of polymers and copolymers of polyacrylonitrile, such as available commercially under the trademarks such as Orlon®, Creslan® and Acrilan®.

The cellulosic fibers can be any hydrophilic, synthetic cellulose-based fiber such as viscose rayon but preferably are of solvent spun cellulose such as "lyocell" sold by Courtaulds Corporation.

In this use, it is preferred that the acrylic fibers in the first layer contain a biocide. There are a number of potential biocides that can be used in the present invention. Preferably the biocide is mixed into the polymer solution thus being permanently in the vest 10. One example of a biocide that may be used in this manner is commercially known as Microban™, which can be introduced in the acrylic polymer solution during spinning. Biocide-containing acrylic fibers are commercially available, for example, Biofresh™ from Sterling Fibers Company (Pensacola, Fla.). For use in hospital applications, it is preferred that a biocide, or antimicrobial agent, be used that kills MRSA bacteria, i.e., methicillin resistant *Staphyloccocus aureus*.

The absorbent spunlaced fabric forming the first layer of this present invention can be prepared by methods known in the art as taught, for example, in U.S. Pat. No. 3,485,709 (Evans) and U.S. Pat. No. 5,093,190 (Kwok et al.), the entire disclosures of which are incorporated herein by way of reference.

A second layer 33 of fabric is provided over the first layer 32 which is much heavier and thicker than either of the inner or first layers 31 and 32, but is very open and breathable. The second layer 33 is described as a cushion-like, high loft fabric because it is dimensionally thick while being open with a resilient or springy quality much like that of a sponge without the liquid absorbance of a sponge. The second layer 33 is preferably formed of 5 to 12 ounce per square yard needle punched fabric made from about a 10 to 30 denier fiber. The second layer 33 preferably tends to be somewhat stiff but has a springy, cushion-like feel which when pressed onto the patient will give support but will allow some movement within the confines of an outermost layer 34, described below. The second layer 33, as noted above, is quite open to allow air to pass easily therethrough to provide ready convection of body heat and moisture from the patient.

The outermost layer 34 is preferably a non-absorbing protective fabric having high abrasion resistance and which forms the outer surface of the vest 10. This outermost layer 34 is preferably strong to hold the vest tight to the patient as desired by the medical practitioner with minimal stretch. It should also withstand the wear and tear of being worn by a patient without further cover. It should be understood that a further cover could be provided, or the vest could be constructed of a combination of the first three layers 31, 32, and 33 in the form of a liner for a separate cover similar to the outermost layer 34. The seperate cover would thereby be a separate piece which would be applied over the liner.

As these materials overlie the patient, moisture in the form of perspiration contacts the inner layer 31 and is wicked laterally and through to the first layer 32. The moisture is transported through the first layer 32 and evaporated into the open needle punched second layer 33.

One particular advantage of the present invention is that the spun-in antimicrobial agent in the first layer provides an antimicrobial migration effect into the entire composite and keeps the odor problem under control.

The foregoing description and drawings were intended to explain and describe the invention so as to contribute to the public base of knowledge. In exchange for this contribution of knowledge and understanding, exclusive rights are sought and should be respected. The scope of such exclusive rights should not be limited or narrowed in any way by the particular details and preferred arrangements that may have been shown. Clearly, the scope of any patent rights granted on this application should be measured and determined by the claims that follow.

We claim:

1. A lining material for contacting the body of a wearer under a stabilizing device such as an orthopedic cast, the lining material comprising:
    a first layer of a spunlaced water-absorbent nonwoven fabric comprised of a blend of polymeric and synthetic cellulosic fibers wherein the polymeric fibers provide loft to the nonwoven and the synthetic cellulosic are hydrophilic; and
    a second layer of cushion-like, high loft open material having a basis weight of at least 5.0 ounces per square yard to allow liquid absorbed into the first layer to be transported through to the atmosphere.

2. The lining material according to claim 1, wherein the second layer is thicker than said first layer.

3. The lining material according to claim 1, herein the second layer comprises needle punched nonwoven material.

4. The lining material according to claim 3, wherein the needle punched second layer material comprises polyester fiber of at least 8 denier.

5. The lining material according to claim 4, wherein the needle punched second layer comprises polyester fiber of at least 12 denier.

6. The lining material according to claim 1, wherein the first layer includes a biocide to reduce bacterial growth.

7. The lining material according to claim 6, wherein the biocide is spun into the polymeric fibers.

8. The lining material according to claim 1, wherein the polymeric fibers comprise polypropylene polymer.

9. The lining material according to claim 1, wherein the polymeric fibers comprise acetate polymer.

10. The lining material according to claim 1, wherein the polymeric fibers comprise acrylic polymer.

11. The lining material according to claim 1, further including an inner fabric layer positioned inside the first layer to be in contact with the wearer's skin, wherein the inner fabric layer comprises fibers having a cross section adapted for improved wicking properties.

12. The lining material according to claim 11, wherein a substantial portion of the fibers of the inner fabric layer have a scalloped-oval cross section.

13. An orthopedic stabilization device comprising:
    a first layer of a spunlaced water-absorbent nonwoven fabric comprised of a blend of polymeric and synthetic cellulosic fibers wherein the polymeric fibers provide loft to the nonwoven and the synthetic cellulosic are hydrophilic;
    a second layer of cushion-like, high loft open material having a basis weight of at least 5.0 ounces per square yard to allow liquid absorbed into the first layer to be transpired through to the atmosphere; and
    a third layer comprising an abrasion resistant material suited for compressing the first and second layers against the wearer while stabilizing or immobilizing a portion of the wearer's body.

14. The orthopedic stabilization device according to claim 13, further including an inner fabric layer positioned inside the first layer so as to be in contact with the wearer's skin, wherein the inner fabric layer comprises fibers having a scalloped-oval cross section.

15. The orthopedic stabilization device according to claim 14, wherein the first layer includes a biocide spun into the polymer fiber.

* * * * *